US009545337B2

(12) United States Patent
Yalamanchili et al.

(10) Patent No.: US 9,545,337 B2
(45) Date of Patent: Jan. 17, 2017

(54) ACOUSTIC STREAMING GLAUCOMA DRAINAGE DEVICE

(71) Applicant: Alcon Research, Ltd., Fort Worth, TX (US)

(72) Inventors: Satish Yalamanchili, Irvine, CA (US); Mikhail Ovchinnikov, Dana Point, CA (US); Jianbo Zhou, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 268 days.

(21) Appl. No.: 14/019,234

(22) Filed: Sep. 5, 2013

(65) Prior Publication Data

US 2014/0276343 A1   Sep. 18, 2014

Related U.S. Application Data

(60) Provisional application No. 61/792,435, filed on Mar. 15, 2013.

(51) Int. Cl.
*A61M 5/00*   (2006.01)
*A61F 9/007*   (2006.01)

(52) U.S. Cl.
CPC ................. *A61F 9/00781* (2013.01)

(58) Field of Classification Search
CPC ................. A61M 27/002; A61M 2210/0612; A61F 9/00781; A61F 9/007; A61B 5/0084
USPC . 604/8, 9, 107, 108; 623/4.1, 1.12; 424/422, 424/423
See application file for complete search history.

(56) References Cited

U.S. PATENT DOCUMENTS

| | | | |
|---|---|---|---|
| 121,697 | A | 12/1871 | Wheatland |
| 294,334 | A | 2/1884 | Reed et al. |
| 351,159 | A | 10/1886 | Brengel |
| 865,631 | A | 9/1907 | Cotter |
| 1,061,142 | A | 5/1913 | Tesla |
| 1,061,206 | A | 5/1913 | Tesla |
| 1,874,667 | A | 8/1932 | Wada |
| 2,015,123 | A | 9/1935 | Pennell |
| 2,121,936 | A | 6/1938 | Thomas |
| 2,386,765 | A | 10/1945 | Adams et al. |
| 2,536,836 | A | 1/1951 | Bowling |
| 2,623,725 | A | 12/1952 | Sands |
| 2,755,816 | A | 7/1956 | Collins |
| 2,987,004 | A | 6/1961 | Murray |

(Continued)

FOREIGN PATENT DOCUMENTS

| | | |
|---|---|---|
| CA | 2316640 | 2/2001 |
| CA | 2649867 A1 | 6/2001 |

(Continued)

OTHER PUBLICATIONS

International Search Report for PCT/US2010/058931, filed Dec. 3, 2010, Publication No. 2011071775, Published Jun. 16, 2011, 2 pages.

(Continued)

*Primary Examiner* — Philip R Wiest
(74) *Attorney, Agent, or Firm* — Haynes & Boone, LLP (57) ABSTRACT

An acoustic streaming valve arrangement induces flow in a glaucoma drainage device. The arrangement may include a selectively vibrating flow generator having a sharp edge and a driving device configured to selectively vibrate the flow generator to create a streaming fluid flow in a direction away from the sharp edge.

19 Claims, 5 Drawing Sheets

(56) References Cited

U.S. PATENT DOCUMENTS

| | | |
|---|---|---|
| 3,085,589 A | 4/1963 | Sands |
| 3,191,807 A | 6/1965 | Rodrigues |
| 3,336,942 A | 8/1967 | Keith et al. |
| 3,447,478 A | 6/1969 | Clemens |
| 3,487,784 A | 1/1970 | Rafferty et al. |
| 3,561,471 A | 2/1971 | Sands |
| 3,567,345 A | 3/1971 | Ballentine |
| 3,589,363 A | 6/1971 | Banko et al. |
| 3,693,613 A | 9/1972 | Kelman |
| 3,724,974 A | 4/1973 | Molimard |
| 3,756,270 A | 9/1973 | Fonseca et al. |
| 3,784,323 A | 1/1974 | Sausse |
| 3,818,913 A | 6/1974 | Wallach |
| 3,882,872 A | 5/1975 | Douvas et al. |
| 3,930,505 A | 1/1976 | Wallach |
| 3,996,935 A | 12/1976 | Banko |
| 4,140,118 A | 2/1979 | Jassawalla |
| 4,187,057 A | 2/1980 | Xanthopoulos |
| 4,205,948 A | 6/1980 | Jones |
| 4,255,081 A | 3/1981 | Oklejas et al. |
| 4,392,794 A | 7/1983 | Foxcroft |
| 4,405,289 A | 9/1983 | Nakashima |
| 4,479,761 A | 10/1984 | Bilstad et al. |
| 4,493,706 A | 1/1985 | Borsanyi et al. |
| 4,496,342 A | 1/1985 | Banko |
| 4,530,647 A | 7/1985 | Uno |
| 4,537,561 A | 8/1985 | Xanthopoulos |
| 4,657,490 A | 4/1987 | Abbott |
| 4,661,093 A | 4/1987 | Beck et al. |
| 4,684,328 A * | 8/1987 | Murphy ................ 417/410.2 |
| 4,705,500 A | 11/1987 | Reimels et al. |
| 4,713,051 A | 12/1987 | Steppe et al. |
| 4,758,238 A | 7/1988 | Sunblom et al. |
| 4,764,165 A | 8/1988 | Reimels et al. |
| 4,768,547 A | 9/1988 | Danby et al. |
| 4,790,726 A | 12/1988 | Balkau et al. |
| 4,798,580 A | 1/1989 | DeMeo et al. |
| 4,838,865 A | 6/1989 | Flank et al. |
| 4,854,825 A | 8/1989 | Bez et al. |
| 4,861,332 A | 8/1989 | Parisi |
| 4,904,238 A | 2/1990 | Williams |
| 4,909,710 A | 3/1990 | Kaplan et al. |
| 4,909,713 A | 3/1990 | Finsterwald et al. |
| 4,921,477 A | 5/1990 | Davis |
| 4,923,375 A | 5/1990 | Ejlersen |
| 4,935,005 A | 6/1990 | Haines |
| 4,963,131 A | 10/1990 | Wortrich |
| 5,038,965 A | 8/1991 | Cater |
| 5,041,096 A | 8/1991 | Beuchat et al. |
| 5,044,902 A | 9/1991 | Malbec |
| 5,046,486 A | 9/1991 | Grulke et al. |
| 5,062,775 A | 11/1991 | Orth |
| 5,106,366 A | 4/1992 | Steppe |
| 5,106,367 A | 4/1992 | Ureche et al. |
| 5,167,620 A | 12/1992 | Ureche et al. |
| 5,185,002 A | 2/1993 | Venturini |
| 5,195,960 A | 3/1993 | Hossin et al. |
| 5,207,647 A | 5/1993 | Phelps |
| 5,257,917 A | 11/1993 | Minarik |
| 5,263,830 A | 11/1993 | Goi et al. |
| 5,267,956 A | 12/1993 | Beuchat |
| 5,273,517 A | 12/1993 | Barone et al. |
| 5,302,093 A | 4/1994 | Owens et al. |
| 5,316,440 A | 5/1994 | Kijima et al. |
| 5,342,181 A | 8/1994 | Schock et al. |
| 5,350,357 A | 9/1994 | Kamen et al. |
| 5,364,342 A | 11/1994 | Beuchat et al. |
| 5,392,653 A | 2/1995 | Zanger et al. |
| 5,403,277 A | 4/1995 | Dodge et al. |
| 5,429,485 A | 7/1995 | Dodge |
| 5,429,601 A | 7/1995 | Conley et al. |
| 5,429,602 A | 7/1995 | Hauser |
| 5,443,370 A | 8/1995 | Wang |
| 5,460,490 A | 10/1995 | Carr et al. |
| 5,462,416 A | 10/1995 | Dennehey et al. |
| 5,470,312 A | 11/1995 | Zanger et al. |
| 5,476,448 A | 12/1995 | Urich |
| 5,484,239 A | 1/1996 | Chapman et al. |
| 5,487,747 A | 1/1996 | Stagmann et al. |
| 5,515,930 A | 5/1996 | Glaser |
| 5,518,378 A | 5/1996 | Neftel et al. |
| 5,533,976 A | 7/1996 | Zaleski et al. |
| 5,542,918 A | 8/1996 | Atkinson |
| 5,554,013 A | 9/1996 | Owens et al. |
| 5,575,632 A | 11/1996 | Morris et al. |
| 5,588,815 A | 12/1996 | Zaleski et al. |
| 5,616,118 A * | 4/1997 | Ahmed ................ 604/8 |
| 5,630,711 A | 5/1997 | Luedtke et al. |
| 5,674,226 A | 10/1997 | Doherty et al. |
| 5,688,112 A | 11/1997 | Garay |
| 5,697,910 A | 12/1997 | Cole et al. |
| 5,705,018 A | 1/1998 | Hartley |
| 5,709,539 A | 1/1998 | Hammer et al. |
| 5,712,543 A | 1/1998 | Sjostrom |
| 5,733,256 A | 3/1998 | Costin |
| 5,746,708 A | 5/1998 | Giesler et al. |
| 5,746,719 A | 5/1998 | Farra et al. |
| 5,759,017 A | 6/1998 | Patton et al. |
| 5,782,634 A | 7/1998 | Lingenhole et al. |
| 5,788,667 A | 8/1998 | Stoller |
| 5,810,765 A | 9/1998 | Oda |
| 5,827,218 A | 10/1998 | Nguyen et al. |
| 5,853,386 A | 12/1998 | Davis et al. |
| 5,879,363 A | 3/1999 | Urich |
| 5,897,300 A | 4/1999 | Luedtke |
| 5,897,524 A | 4/1999 | Wortrich et al. |
| 5,906,598 A | 5/1999 | Giesler et al. |
| 5,910,110 A | 6/1999 | Bastable |
| 5,927,956 A | 7/1999 | Lim et al. |
| 5,951,581 A | 9/1999 | Saadat et al. |
| 5,972,012 A | 10/1999 | Ream et al. |
| 5,989,212 A | 11/1999 | Sussman et al. |
| 5,996,634 A | 12/1999 | Dennehey et al. |
| 5,997,499 A | 12/1999 | Sussman et al. |
| 6,012,999 A | 1/2000 | Patterson |
| 6,042,586 A | 3/2000 | Kawano et al. |
| 6,058,779 A | 5/2000 | Cole |
| 6,080,128 A | 6/2000 | Sussman et al. |
| 6,109,895 A | 8/2000 | Ray et al. |
| 6,110,162 A | 8/2000 | Sussman et al. |
| 6,117,149 A | 9/2000 | Sorensen et al. |
| 6,129,699 A | 10/2000 | Haight et al. |
| 6,179,805 B1 | 1/2001 | Sussman et al. |
| 6,217,543 B1 | 4/2001 | Anis et al. |
| 6,241,700 B1 | 6/2001 | Leukanech |
| 6,270,326 B1 | 8/2001 | Kuriyama |
| 6,293,926 B1 | 9/2001 | Sorensen et al. |
| 6,296,460 B1 | 10/2001 | Smith |
| 6,416,293 B1 | 7/2002 | Bouchard et al. |
| 6,491,661 B1 | 12/2002 | Boukhny et al. |
| 6,527,765 B2 | 3/2003 | Kelman et al. |
| 6,551,080 B2 | 4/2003 | Andersen et al. |
| 6,572,349 B2 | 6/2003 | Sorensen et al. |
| 6,599,277 B2 | 7/2003 | Neubert |
| 6,605,054 B2 | 8/2003 | Rockley |
| 6,655,934 B2 | 12/2003 | Mittelstein et al. |
| 6,689,146 B1 | 2/2004 | Himes |
| 6,723,065 B2 | 4/2004 | Kishimoto |
| 6,749,403 B2 | 6/2004 | Bryant et al. |
| 6,811,386 B2 | 11/2004 | Hedington et al. |
| 6,814,547 B2 | 11/2004 | Childers et al. |
| 6,868,987 B2 | 3/2005 | Hedington |
| 6,958,058 B1 | 10/2005 | Hunter, Sr. et al. |
| 6,962,488 B2 | 11/2005 | Davis et al. |
| 7,063,688 B2 | 6/2006 | Say |
| 7,070,574 B2 | 7/2006 | Jackson et al. |
| 7,144,383 B2 | 12/2006 | Arnett et al. |
| 7,150,607 B2 | 12/2006 | Pelmulder et al. |
| 7,238,164 B2 | 7/2007 | Childers et al. |
| 7,273,359 B2 | 9/2007 | Blight et al. |
| 7,276,060 B2 | 10/2007 | Madden |
| 7,393,189 B2 | 7/2008 | Davis et al. |
| 7,445,436 B2 | 11/2008 | Mittelstein et al. |
| 7,540,855 B2 | 6/2009 | Lumpkin et al. |

(56) References Cited

U.S. PATENT DOCUMENTS

| | | |
|---|---|---|
| 7,604,610 B2 | 10/2009 | Shener et al. |
| 7,632,080 B2 | 12/2009 | Tracey et al. |
| 7,645,127 B2 | 1/2010 | Hagen et al. |
| 7,695,242 B2 | 4/2010 | Fuller |
| 7,758,515 B2 | 7/2010 | Hibner |
| 7,775,780 B2 | 8/2010 | Hopkins et al. |
| 7,862,540 B2 | 1/2011 | Dacquay et al. |
| 7,967,777 B2 | 6/2011 | Edwards et al. |
| 8,070,712 B2 | 12/2011 | Muri et al. |
| 8,087,909 B2 | 1/2012 | Shener |
| 8,162,633 B2 | 4/2012 | Edwards |
| 8,579,929 B2 | 11/2013 | Mackool et al. |
| 8,617,106 B2 | 12/2013 | Zacharias |
| 9,132,034 B2 | 9/2015 | Dos Santos |
| 2001/0016706 A1 | 8/2001 | Leukanech et al. |
| 2002/0062105 A1 | 5/2002 | Tanner et al. |
| 2002/0077587 A1 | 6/2002 | Boukhny et al. |
| 2003/0108429 A1 | 6/2003 | Angelini et al. |
| 2003/0199803 A1 | 10/2003 | Robinson et al. |
| 2004/0122381 A1 | 6/2004 | Arnold |
| 2004/0253129 A1 | 12/2004 | Sorensen et al. |
| 2005/0049539 A1 | 3/2005 | O'Hara, Jr. et al. |
| 2005/0070859 A1 | 3/2005 | Cull et al. |
| 2005/0100450 A1 | 5/2005 | Bryant et al. |
| 2005/0271531 A1 | 12/2005 | Brown, Jr. et al. |
| 2006/0000925 A1 | 1/2006 | Maher et al. |
| 2006/0093989 A1 | 5/2006 | Hahn et al. |
| 2006/0110274 A1 | 5/2006 | Gottschalk |
| 2006/0122556 A1 | 6/2006 | Kumar et al. |
| 2006/0245964 A1 | 11/2006 | Koslov |
| 2006/0253194 A1 | 11/2006 | Dial |
| 2007/0078370 A1 | 4/2007 | Shener et al. |
| 2007/0078379 A1 | 4/2007 | Boukhny et al. |
| 2007/0100316 A1 | 5/2007 | Traxinger |
| 2007/0135760 A1 | 6/2007 | Williams |
| 2007/0217919 A1 | 9/2007 | Gordon et al. |
| 2007/0278155 A1 | 12/2007 | Lo |
| 2007/0287959 A1 | 12/2007 | Walter et al. |
| 2008/0097320 A1 | 4/2008 | Moore et al. |
| 2008/0112828 A1 | 5/2008 | Muri et al. |
| 2008/0114289 A1 | 5/2008 | Muri et al. |
| 2008/0114291 A1 | 5/2008 | Muri et al. |
| 2008/0114301 A1 | 5/2008 | Bandhauer et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0200878 A1 | 8/2008 | Davis et al. |
| 2008/0220092 A1 | 9/2008 | Dipierro et al. |
| 2008/0240951 A1 | 10/2008 | Demash et al. |
| 2008/0247892 A1 | 10/2008 | Kawasumi |
| 2009/0012460 A1 | 1/2009 | Steck et al. |
| 2009/0035164 A1 | 2/2009 | Edwards |
| 2009/0060756 A1 | 3/2009 | Jones |
| 2009/0084718 A1 | 4/2009 | Prisco et al. |
| 2009/0246035 A1 | 10/2009 | Patzer |
| 2009/0299272 A1 | 12/2009 | Hopping et al. |
| 2009/0317271 A1 | 12/2009 | Gill et al. |
| 2010/0056979 A1* | 3/2010 | Smedley et al. ............ 604/9 |
| 2010/0125257 A1 | 5/2010 | Perkins et al. |
| 2010/0130920 A1 | 5/2010 | Lo et al. |
| 2010/0130934 A1 | 5/2010 | Rochat |
| 2010/0145259 A1 | 6/2010 | Nash et al. |
| 2010/0191178 A1 | 7/2010 | Ross et al. |
| 2010/0228146 A1 | 9/2010 | Hibner |
| 2010/0241044 A1 | 9/2010 | Caleffi et al. |
| 2010/0280435 A1 | 11/2010 | Raney et al. |
| 2010/0286791 A1 | 11/2010 | Goldsmith |
| 2011/0092891 A1 | 4/2011 | Gerg et al. |
| 2011/0137231 A1 | 6/2011 | Sorensen et al. |
| 2011/0144567 A1 | 6/2011 | Sorensen et al. |
| 2011/0184374 A1 | 7/2011 | Gao et al. |
| 2012/0041358 A1 | 2/2012 | Mann et al. |
| 2012/0083728 A1 | 4/2012 | Sorensen et al. |
| 2013/0019968 A1 | 1/2013 | Liebing |

FOREIGN PATENT DOCUMENTS

| | | |
|---|---|---|
| CA | 2743969 A1 | 3/2005 |
| CA | 2649867 C | 6/2010 |
| CN | 101023898 | 8/2007 |
| CN | 200991440 | 12/2007 |
| DE | 3809582 | 10/1989 |
| DE | 19749358 | 5/1998 |
| DE | 19711675 | 10/1998 |
| DE | 19856744 | 6/2000 |
| DE | 10034711 B4 | 2/2002 |
| DE | 10034711 A1 | 4/2006 |
| DE | 102007044790 | 4/2009 |
| EP | 0200448 | 5/1986 |
| EP | 0320963 | 6/1989 |
| EP | 0362822 | 4/1990 |
| EP | 518050 A1 | 12/1992 |
| EP | 518050 B1 | 7/1996 |
| EP | 0944404 | 9/1999 |
| EP | 1140257 | 10/2001 |
| EP | 1258260 | 11/2002 |
| EP | 964711 | 4/2005 |
| EP | 1810702 | 7/2007 |
| EP | 2173404 | 4/2010 |
| EP | 2365220 | 9/2011 |
| EP | 2509659 | 10/2012 |
| FR | 2466641 | 4/1981 |
| FR | 2797190 | 2/2001 |
| GB | 2029514 | 3/1980 |
| GB | 2174763 | 11/1986 |
| GB | 2190145 | 5/1990 |
| JP | 60001391 | 1/1985 |
| JP | 63-290564 | 11/1988 |
| JP | 02070987 | 3/1990 |
| JP | H03-164586 | 7/1991 |
| JP | 2002-248117 | 9/2002 |
| JP | 3785643 | 6/2006 |
| JP | 2007-507636 | 3/2007 |
| JP | 2007-198382 | 8/2007 |
| JP | 2007-247646 | 9/2007 |
| JP | 2008-546501 | 12/2008 |
| RU | 2197277 | 1/2003 |
| RU | 2241887 | 12/2004 |
| SU | 1533696 | 1/1990 |
| SU | 1590649 | 9/1990 |
| WO | WO 9517597 | 6/1995 |
| WO | WO 98/18507 | 5/1998 |
| WO | WO 98/24495 | 6/1998 |
| WO | WO 99/38549 | 8/1999 |
| WO | WO 00/22995 | 4/2000 |
| WO | WO 00/33898 | 6/2000 |
| WO | WO 00/53136 | 9/2000 |
| WO | WO 03 073969 | 9/2003 |
| WO | WO 2005009511 A2 | 2/2005 |
| WO | WO 2005009511 A3 | 6/2005 |
| WO | WO 2008/131357 | 10/2008 |
| WO | WO 2009/005900 | 1/2009 |
| WO | WO 2009/146913 A2 | 12/2009 |
| WO | WO 2009/146913 A3 | 2/2010 |
| WO | WO 2010/061863 | 6/2010 |
| WO | WO 2010/129128 | 11/2010 |
| WO | WO 2011/071775 | 6/2011 |
| WO | WO 2012048261 A2 | 4/2012 |
| WO | WO 2012048261 A3 | 6/2012 |

OTHER PUBLICATIONS

Written Opinion of the International Searching Authority, International Application No. PCT/US2010/058931, Feb. 1, 2011, 4 pages.

International Search Report for PCT/US2010/059032, filed Dec. 6, 2010, Publication No. 2011075332, Published Jun. 23, 2011, 2 pages.

Written Opinion of the International Searching Authority, International Application No. PCT/US2010/059032, Jan. 31, 2011, 5 pages.

Examiner Edelmira Bosques, Non-Final Office Action, U.S. Appl. No. 12/637,886, Oct. 3, 2011, 11 pages.

(56) References Cited

OTHER PUBLICATIONS

Supplementary European Search Report for Application No. EP 10836456.3, Publication No. EP 2509659, Published Oct. 17, 2012, dated Mar. 20, 2013, 5 pages.
Supplementary European Search Report for Application No. EP 10838118.7, Publication No. EP2512554, Published Oct. 24, 2012, dated Apr. 15, 2013, 6 pages.
Milutinovic, et al., "Phacoemulsification Fluidics System Having a Single Pump Head," U.S. Appl. No. 12/818,682, filed Jun. 18, 2010, 28 pages.
International Searching Authority, Written Opinion of the International Searching Authority, International Application No. PCT/US2010/030168, Aug. 3, 2010, 8 pages.
International Search Report and Written Opinion of the International Searching Authority, International Application No. PCT/US2014/027271, filed Mar. 14, 2014, dated Jul. 28, 2014, 8 pages.
International Search Report and Written Opinion of the International Searching Authority, International Application No. PCT/US2014/027233, filed Mar. 14, 2014, dated Jul. 31, 2014, 10 pages.
International Search Report and Written Opinion of the International Searching Authority, International Application No. PCT/US2014/027307, filed Mar. 14, 2014, dated Jul. 30, 2014, 7 pages.
Sorensen, Gary, Phacoemulsification Hand Piece with Integrated Aspiration Pump, U.S. Appl. No. 13/325,549, filed Dec. 14, 2011, 18 pages.
http://www.advancedfluid.com/discflo/concepts.htm. Web archive dated Aug. 8, 2008, 3 pages.
Ovchinnikov et al., Acoustic Streaming of a Sharp Edge, Journal of Acoustical Society of America, 136 (1), Jul. 2014, pp. 22-29.
Mednikov, E. P. et al., Experimental study of intense acoustic streaming, Sov. Phys. Acoust., Mar.-Apr. 1975, p. 152-154, vol. 21, No. 2.
Nyborg, W. L., Acoustic Streaming near a Boundary*, The Journal of the Acoustical Society of America, Dec. 16, 1957, pp. 329-339, vol. 30, No. 4.
Nyborg, W. L., Acoustic Streaming due to Attenuated Plane Waves, The Journal of the Acoustical Society of America, Sep. 30, 1952, pp. 68-75, vol. 25.
Barenblatt, G. I., Scaling, self-similarity, and intermediate asymptotics, 1966, pp. iv-15, Cambridge University Press, Cambridge.
Boluriaan, S. et al., Acoustic streaming: from Rayleigh to today, aeroacoustics, 2003, pp. 255-292, vol. 2, No. 3 & 4.
Faraday, M., On a Peculiar Class of Acoustical Figures; and on Certain Forms Assumed by Groups of Particles upon Vibrating Elastic Surface, Philosophical Transactions of the Royal Society of London, 1831, pp. 299-340, vol. 121.
Holtsmark et. al., Boundary Layer Flow near a Cylindrical Obstacle in an Oscillating Incompressible Fluid, J. Acoust. Soc. Am., 1954, p. 102, 26.
Ingard, U. et al., Acoustic Circulation Effects and the Nonlinear Impedance of Orifices*, The Journal of the Acoustical Society of America, Mar. 1950, pp. 211-218, vol. 22, No. 2.
James, R. D. et al., A round turbulent jet produced by an oscillating diaphragm, Physics of Fluids, Sep. 1996, pp. 2484-2495, vol. 8, No. 9.
Kishimoto, Makoto, MD, Opesaver-Super Irrigation System, Techniques in Ophthalmology, 2006, 5 pages, vol. 4, Issue 1, Lippincott Williams & Wilkins, Shiga, Japan.
Landau, D. et al. (See for example), One-Dimensional Gas Flow, Fluid Dynamics, 1987. pp. 361-413, par. 10, problem 6, Pergamon Press, Oxford.
Lebedeva, I.V., Experimental study of acoustic streaming in the vicinity of orifices, Sov. Phys. Acoust., Jul.-Aug. 1980, pp. 331-333, vol. 26(4), Americal Institute of Physics.
Lighthill, J., Acoustic Streaming, Journal of Sound and Vibration, Jul. 1978, pp. 391-418, 61(3), Academic Press Inc., London.
Loh, B-G et al., Acoustic streaming induced by ultrasonic flexural vibrations and associated enhancement of convective heat transfer, J. Acoust. Soc. Am., Feb. 2002, pp. 875-883, vol. 111, No. 2.
Rayleigh, L., Theory of Sound, 1945, Par. 352, Dover Publications, New York.
Riley, N., On a Sphere Oscillating in a Viscous Fluid, Quart. Journ. Mech. And Applied Math, Jan. 1966, pp. 461-472, vol. 19, Pt. 4.
Riley, N., Oscillatory Viscous Flows. Review and Extension, J. Inst. Maths Applics, Jan. 30, 1967, pp. 419-434, 3.
Riley, N., Acoustic streaming about a cylinder in orthogonal beams, J. Fluid Mech., 1992, pp. 387-394, vol. 242.
Riley, N., Acoustic Streaming, Encyclopedia of Acoustics, 1997, pp. 321-327, vol. 1, ed M. J. Crocker, John Wiley & Sons, Inc., New York.
Stuart, J. T., Double boundary layers in oscillatory viscous flow, J. Fluid Mech., 1966, pp. 673-687, vol. 24, part 4.
Taneda, S., Visualization of Steady Flows Induced by a Circular Cylinder Performing a Rotatory Oscillation about an Eccentric Axis, Journal of the Physical Society of Japan, Nov. 1980, pp. 2038-2041, vol. 49, No. 5.
Zacharias, J. et al., Fluid dynamics, cavitation, and tip-to-tissue interaction of longitudinal and torsional ultrasound modes during phacoemulsification, presentation at ASCRS meeting, 2010, pp. 611-616. Boston.
European Application No. 13863111.4, Extended European Search Report mailed Jul. 14, 2015, 6 pgs.
International Application No. PCT/US2010/058931, International Preliminary Report on Patentability issued Jun. 12, 2012, 5 pgs.
International Application No. PCT/US2014/027271, International Preliminary Report on Patentability issued Sep. 15, 2015, 6 pgs.
International Application No. PCT/US2014/027307, International Preliminary Report on Patentability issued Sep. 15, 2015, 5 pgs.
International Application No. PCT/US2010/059032, International Preliminary Report on Patentability issued Jun. 19, 2012, 6 pgs.
International Application No. PCT/US2013/064202, International Preliminary Report on Patentability issued Jun. 16, 2015, 6 pgs.
International Application No. PCT/US2014/027233, International Preliminary Report on Patentability issued Sep. 15, 2015, 8 pgs.
International Application No. PCT/US2017-064416, International Preliminary Report on Patentability issued Jun. 7, 2016, 8 pgs.
International Application No. PCT/US2015/026293, International Search Reporting and Written Opinion mailed Jul. 23, 2015, 10 pgs.
International Application No. PCT/US2010/041786, International Search Report mailed Oct. 28, 2010, 5 pgs.
International Application No. PCT/US2015/037783, International Search Report mailed Sep. 28, 2015, 4 pgs.
International Application No. PCT/US2009-057675, Written Opinion mailed Mar. 25, 2011, 5 pgs.
International Application No. PCT/US2010/041786, Written Opinion mailed Oct. 28, 2010, 6 pgs.
International Application No. PCT/US2015/037783, Written Opinion mailed Sep. 28, 2010, 5 pgs.

* cited by examiner

ACOUSTIC STREAMING GLAUCOMA DRAINAGE DEVICE

CROSS-REFERENCE TO RELATED APPLICATIONS

This application claims the benefit of U.S. Provisional Application No. 61/792,435, filed Mar. 15, 2013 the entire contents of which are incorporated herein by reference.

TECHNICAL FIELD

The present disclosure relates generally to devices, systems, and methods for treating an ocular condition. More particularly, the present disclosure relates generally to implantable ocular devices configured to use acoustic streaming to treat an ocular condition.

BACKGROUND

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

Figure 1:
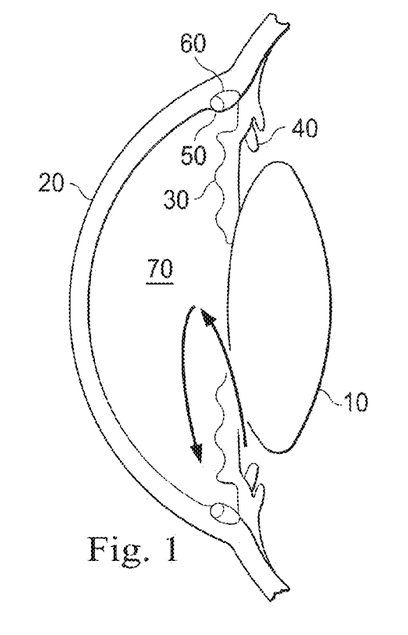
FIG. 1 is a diagram of the front portion of an eye.

FIG. 1 is a diagram of the front portion of an eye that helps to explain the processes of glaucoma. In FIG. 1, representations of the lens 10, cornea 20, iris 30, ciliary body 40, trabecular meshwork 50, Schlemm's canal 60, and anterior chamber 70 are pictured. Anatomically, the anterior segment of the eye includes the structures that cause elevated IOP which may lead to glaucoma. Aqueous humor fluid is produced by the ciliary body 40 which lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber 70. The trabecular meshwork 50 seems to act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber 70. The two arrows in the anterior segment of FIG. 1 show the flow of aqueous humor from the ciliary bodies 40, over the lens 10, over the iris 30, through the trabecular meshwork. 50, and into Schlemm's canal 60 and its collector channels.

SUMMARY

In an exemplary aspect, the present disclosure is directed to an acoustic streaming valve arrangement for inducing flow in a glaucoma drainage device. The arrangement may include a selectively vibrating flow generator having a sharp edge; and a driving device configured to selectively vibrate the flow generator to create a streaming fluid flow in a direction away from the sharp edge.

In an aspect, the flow generator comprises two nonparallel surfaces forming an angle. In an aspect, the two nonparallel surfaces converge to form the sharp edge. In an aspect, the sharp edge has an angle of 90 degrees or less. In an aspect, the driving device is configured to vibrate the flow generator at the resonance frequency of the flow generator. In an aspect, the arrangement further comprises a flexible portion deflectable by streaming fluid flow to open a valve.

In an exemplary aspect, the present disclosure is directed to an implantable glaucoma drainage system that comprises an inlet passageway and an outlet passageway and a valve portion disposed between the inlet and outlet passageways to regulate the passageway of fluid from the inlet passageway to the outlet passageway. The valve portion may comprise an acoustic streaming valve arrangement configured to open or close the valve portion, as well as actively pump the fluid through the valve.

In an aspect, the acoustic streaming valve arrangement comprises a flow generator and a driving device configured to vibrate the flow generator, the flow generator being disposed in the inlet passageway. In an aspect, the flow generator comprises two nonparallel surfaces forming an angle. In an aspect, the two nonparallel surfaces converge to form a sharp edge, in an aspect, the sharp edge has an angle of 90 degrees or less. In an aspect, the sharp edge is an extending edge. In an aspect, the valve portion comprises a flexible portion deflectable from a neutral condition to a displaced condition, the valve portion inhibiting passage of fluid when the flexible point is a neutral condition and allowing passage of fluid when the flexible portion is in a deflected condition. In an aspect, the flexible portion is a membrane. In an aspect, the acoustic streaming valve arrangement comprises a flow generator and a driving device configured to vibrate the flow generator, the flow generator being disposed in a chamber adjacent the inlet passageway. In an aspect, the driving device is implantable with the flow generator.

In an exemplary aspect, the present disclosure is directed to a method comprising implanting a flow system in an eye of a patient and activating an acoustic streaming valve arrangement forming a part of the flow system to inhibit or allow drainage fluid to flow through the flow system.

In an aspect, activating an acoustic streaming valve arrangement comprises placing a driving device in the proximity of the flow system to induce vibration in a flow generator of the acoustic streaming valve arrangement. In an aspect, activating an acoustic streaming valve arrangement comprises placing the driving device in contact with the flow system to induce vibration in the flow generator. In an aspect, deflecting a flexible portion of the flow system with the acoustic streaming valve arrangement to inhibit or allow drainage fluid to flow through the flow system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to acoustic streaming of a fluid. More particularly, the disclosure relates to an acoustic streaming valve arrangement forming a part of an implantable glaucoma drainage device (GDD) arranged to treat an ocular condition. The acoustic streaming valve arrangement pertains to the use of anomalous streaming of fluid by a vibrating sharp edge in a GDD. In one aspect, the system is designed to act as a valve portion and a pump portion regulating patient LOP. In some aspects, the valve portion includes a membrane that controls flow through the GDD. The amount of force required to open the valve portion may be tuned to correspond to the pressure created by the acoustic streaming valve arrangement. In some aspects, the vibration of the acoustic streaming valve arrangement is activated by an external device controlled by a doctor or a patient. The acoustic pump arrangement may be particularly suited for the treatment of IOP and use in a GDD as it has few or no movable parts making it highly reliable, and it may be easily integrated with other microfluidic circuits. In addition, the acoustic pump arrangement may be relatively easy to manufacture as it may be used/built in conjunction with MEMS (Micro electromechanical systems). It also may be customizable as it may be tunable to a wide range conditions on-the-fly.

Figure 2:
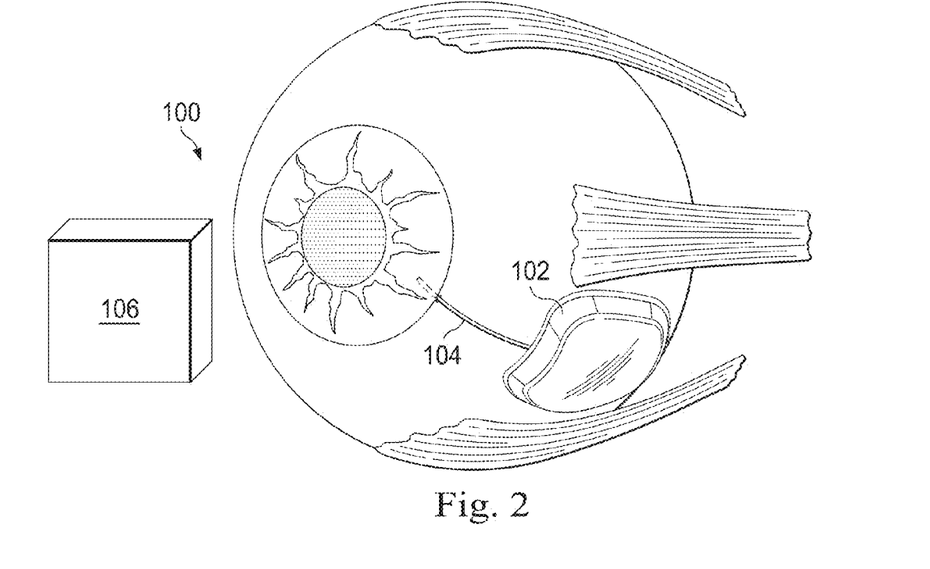
FIG. 2 is an illustration of an exemplary implantable system disposed in the eye in accordance with one embodiment of the present disclosure.

FIG. 2 shows an exemplary implantable system 100 disposed on an eye to treat an ocular condition according to one exemplary aspect of the present disclosure. The implantable system 100 incorporates the acoustic streaming valve arrangement as will be described further below. In the embodiment shown, the implantable system 100 includes a body referred to herein as a plate 102, a drainage tube 104 that extends from the plate 102, and a vibration-generating driving device 106, which in the embodiment in FIG. 2, is an external driving device. The plate 102 is arranged to carry various components of an IOP control system, and may include a valve, pump, transducers or sensors, a processing system and memory, drug delivery components, a power source or other components that may be used to either control the implantable system 100 or otherwise treat ocular conditions. In this exemplary embodiment, the plate 102 includes the acoustic streaming valve arrangement as will be described below.

In some embodiments, the plate 102 is configured to fit at least partially within the subconjunctival space and is sized, for example, within a range between about 15 mm×112 mm to about 30 mm×15 mm and has a thickness less than about 2 mm thick and preferably less than about 1 mm thick. The plate 102 may be formed to the radius of the eye globe (e.g., about 0.5 inches). In some embodiments, the plate 102 is rigid and preformed with a curvature suitable to substantially conform to the eye globe or it may be flexible to conform to the eye globe. Some embodiments have relatively planar outer surfaces. Some of these are small enough that conforming to the eye globe provides little benefit in comfort or implantation technique. The above dimensions are exemplary only, and other sizes and arrangements are contemplated. When implanted, the plate 102 may be located, for example, in the subconjunctival pocket between the conjunctiva and sclera. It may be generally located on an ocular quadrant commonly used for conventional glaucoma drainage devices with plates; that is, it may be centered such that it is equidistant from the neighboring ocular muscles that define the ocular quadrant chosen for implantation.

The drainage tube 104 is sized to bridge the anterior chamber and the plate 102 in the subconjunctival pocket to provide an auxiliary flow path for aqueous humor, bypassing the flow-resistive conventional pathway through the trabecular meshwork and shunting aqueous humor directly to a drainage site. In the example shown, the drainage tube 104 is a single tube having a single lumen. Other embodiments include a plurality of drainage tubes or a plurality of lumens cooperating together to permit fluid to flow through the implantable system 100. The drainage tube 104 is sized to extend from the plate 102 to the anterior chamber of the eye, as shown in FIG. 2. Aqueous humor may drain through the drainage tube 104 from the anterior chamber to and out of the plate 102 to alleviate elevated intraocular pressure conditions.

The vibration-generating driving device 106 is configured to provide an activating force to components carried in the plate 102, and in particular, to the acoustic streaming valve arrangement. In one exemplary embodiment, the driving device is one or more piezoelectric crystals that may form a piezoelectric crystal stack. When alternating current of particular frequency is passed through the piezoelectric crystal stack, the stack vibrates at this frequency that may be used to mechanically drive the acoustic streaming valve arrangement. In other embodiments, the driving device 106 is an inductive device configured to generate a magnetic field that may drive the acoustic streaming valve arrangement. The driving device 106 may be or may form a part of other driving systems. Depending on the driving device 106, the principle of vibration generation can be, for example, piezoelectric or inductive. Other principles of vibration generation are also contemplated.

Figure 3:
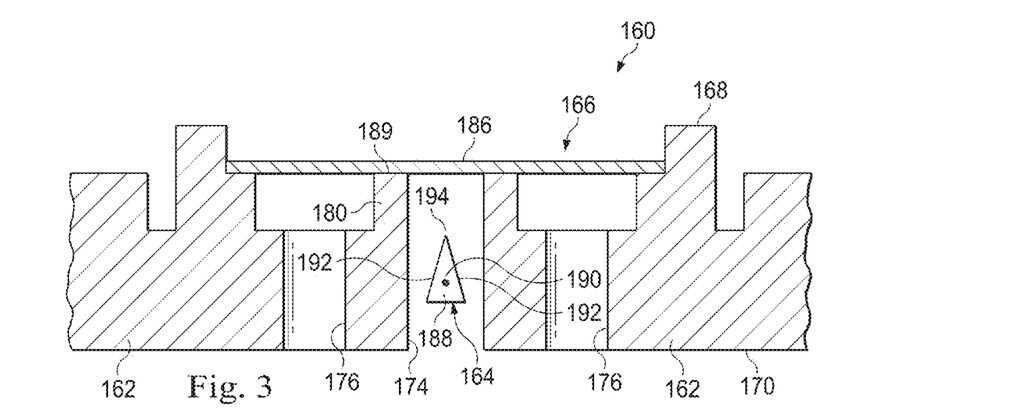
FIG. 3 is an illustration of a cross-sectional view of a flow system carried by the implantable system of FIG. 2 in a closed position according to the principles of the present disclosure.

FIG. 3 shows a cross-sectional view of an exemplary flow system 160 carried by or forming a part of the plate 102. It includes a valve chip 162, a part of an acoustic streaming valve arrangement 164, and a valve portion 166. In this example, the acoustic streaming valve arrangement 164 is configured to draw fluid through an inlet passageway 174 to open the valve portion 166, and is configured so that the fluid can pass the valve portion 166 and be expelled from the valve chip 162 through an outlet passageway 176.

As can be seen in FIG. 3, the valve chip 162 comprises an upper side 168 and a lower side 170 opposite the upper side. At least one inlet passageway 174 and at least one outlet passageway 176 extend from the upper side 168 to the lower side 170. In the embodiment shown, at least two outlet passageways 176 extend from the upper side 168 to the lower side 170. In some embodiments, the outlet passageways 176 may be a circular array of passageways about the inlet passageway 174. The inlet passageway 174 may be in fluid communication with the drainage tube 104 (FIG. 2) and configured to receive aqueous flowing from the drainage tube 104. The outlet passageway 176 permits fluid to exit the flow system 160 for release at a drainage site or for further regulation via additional flow systems.

The valve portion 166 includes a boss portion 180 and a flexible portion 186 that spans the opening of the inlet passageway 174 on the upper side 168. The boss portion 180, in this embodiment, is formed of a portion of the valve chip 162 and includes a seat 189 facing the flexible portion 186 and configured to be selectively and sealingly engaged by the flexible portion 186. Since the seat 189 surrounds the opening of the inlet passageway 174, engagement of the flexible portion with the seat can selectively prevent or inhibit and selectively allow the passage of fluid out the inlet passageway 174 to the outlet passageways 176.

The flexible portion 186 may be a membrane formed of an elastically deformable material including without limitation, materials such as a silicone, silicon nitride, silicone elastomer, polyimide, parylene, and others. In the example shown, the flexible portion 186 is a circular material secured at its periphery to the valve chip 162. In other embodiments, the valve chip 162 and the flexible portion 186 are formed so that the membrane has a non-circular shape, including oval, substantially rectangular, or square, for example. Other shapes are also contemplated.

In the embodiment shown, the flexible portion 186 is configured to be seated against the seat 189 and to prevent fluid passage through the inlet passageway 174 when the flexible portion 186 is in its neutral condition or its natural state. That is, the valve portion 166 is biased to the closed position. When force against the flexible portion 186 exceeds a cracking pressure, i.e., a pressure at which the flexible portion 186 deflects to provide communication between the inlet passageway 174 and the outlet passageways 176 (or exceeds the pressure on the opposing side of the flexible portion), the flexible portion 186 may deflect to permit the passage of fluid through the inlet passageway 174 and over the seat 189.

Figure 4:
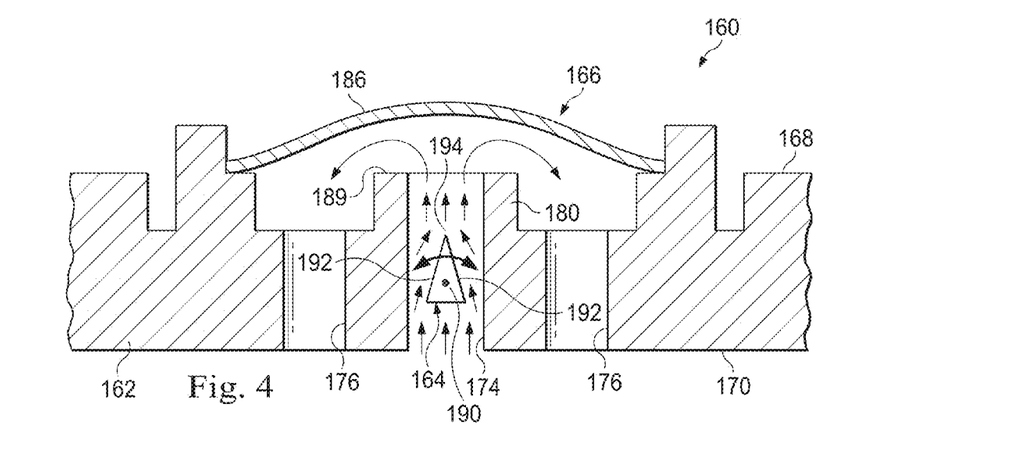
FIG. 4 is an illustration of a cross-sectional view of the flow system in FIG. 3 in an open position according to the principles of the present disclosure.

The acoustic streaming valve arrangement 164 includes a flow generator 188 and the driving device 106 (FIG. 2). When activated, it is configured to crack (i.e., open) the valve portion 166 to allow fluid flow through the system 160. In this embodiment, the flow generator 188 is wedge-shaped microscopic blade and is arranged in the valve chip 162 to vibrate back and forth about a pivot 190 as indicated in FIG. 4. Accordingly, the flow generator 188 includes angled, non-parallel sides 192 converging at a sharp tip, which in this embodiment, is firmed as a sharp edge 194 since it has a protruding length (not shown). Here, the flow generator 188 is disposed directly in the inlet passageway 174, surrounded by fluid, and is operable to create an acoustic streaming of fluid in the direction of the flexible portion 186.

FIG. 3 shows the acoustic streaming valve arrangement 164 in an inactive condition, with the flexible portion 186 engaged against the seat 189, and FIG. 4 shows the acoustic streaming valve arrangement 164 in an activated condition, with the flexible portion 186 spaced apart or deflected from the seat 189. Thus, FIG. 3 shows the valve portion in a closed condition, while FIG. 4 shows the valve portion in an open condition.

Figure 5:
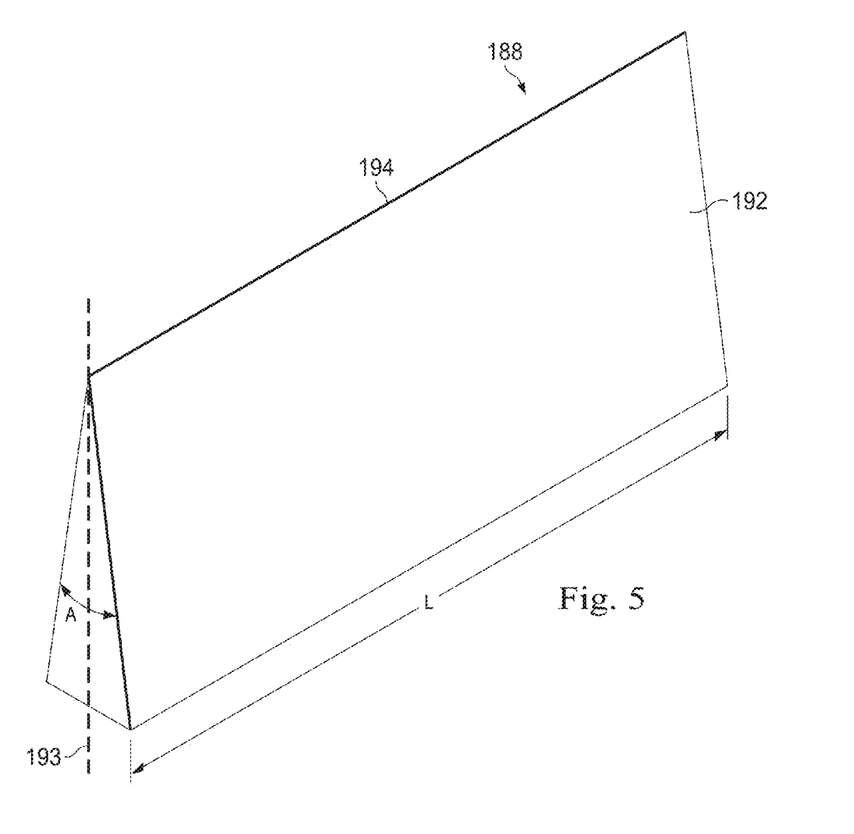
FIG. 5 is an illustration of an exemplary fluid flow generator of the acoustic fluid pump of FIG. 3 according to one aspect of the present disclosure.

The flow generator 188 is shown in greater detail in FIG. 5. With reference to FIGS. 3-5, the flow generator 188 includes angled, non-parallel sides 192 converging at a sharp edge 194, forming a wedge shape. In this embodiment, the sharp edge 194 has a protruding length L, as can be seen in FIG. 5, in the embodiment shown, the two non-parallel sides 192 form an angle A at the sharp edge 194 of about 20 degrees. However, other angles are contemplated. For example, in some embodiments, the angle A forming the sharp edge 194 is formed at an angle between 10 and 90 degrees. In some embodiments, the angle A is formed at an angle between 10 and 60 degrees, and, in some embodiments, angle A is formed at an angle between 15 and 30 degrees. In some embodiments, the angle A is about 30 degrees. Other ranges are also contemplated. The sharper the angle A, the higher the streaming velocities that may be achieved by acoustic streaming valve arrangement 164. Here the sides 192 are symmetrically formed about an axis 193. In FIGS. 3 and 4, the axis 193 aligns with a longitudinal axis of the inlet passageway 174.

Depending on the embodiment and the amount of fluid to be driven by the pump, the flow generator 188 may have a lateral length L in the range of about 50 microns to 5 cm. In other embodiments, the lateral length L is in the range of about 100 microns to 2 cm. While the flow generator 188 may be formed of any material, in one embodiment, it is formed of a steel blade with a 20° sharp edge. In some exemplary embodiments, the flow generator 188 includes two rounded edges so that only the edge 194 is sharp. In one example, the flow generator 188 may form a tear-drop shape in cross-section. The acoustic streaming valve arrangement's role is described below.

Figure 6:
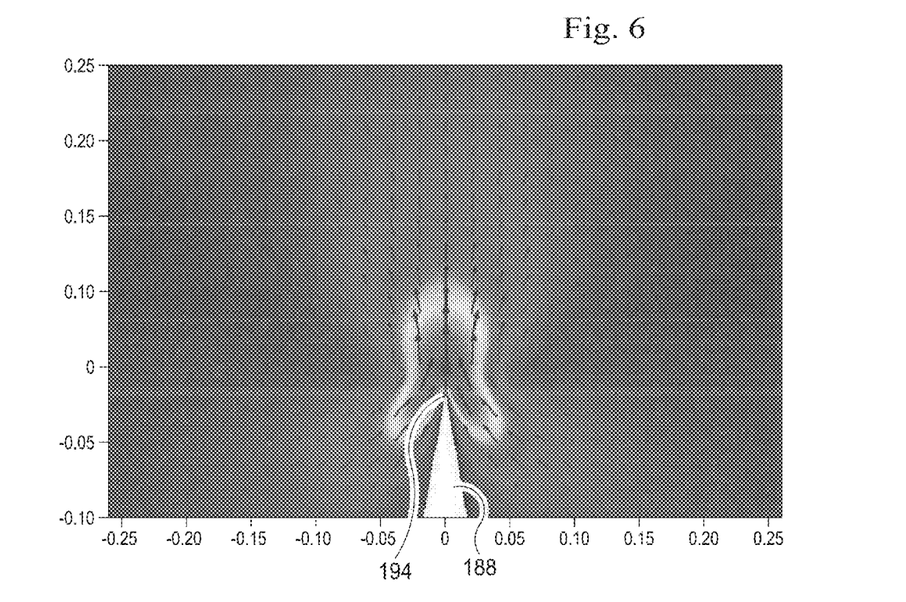
FIG. 6 is an illustration showing the principles of acoustic streaming jet flow obtained using the principles of the present disclosure.

Acoustic streaming is a steady streaming flow that is generated due to oscillatory motion of a sharp-edged body in a fluid. The steady streaming flow is represented in the drawing of FIG. 6. Anomalous jets of fluid are generated by and originate from the vibrating sharp tip or edge 194 of the microscopic wedge or blade forming the flow generator 188. In FIG. 6, the vectors represent the fluid velocity of the jets, and, as can be seen, the velocity is much greater at the tip or sharp edge 194. The velocities of the jets can be as high as 2 m/s and are significantly higher than can be predicted by smooth edges vibrating laterally. The jets of fluid extend substantially perpendicular to the wedge in the same direction as the edge 194, as shown in FIG. 6.

The anomalous streaming occurs at the sharp edge 194 of the wedge-shaped flow generator 188. The blade forming the flow generator 188 vibrates perpendicular to its sharp edge 194 and generates a strong microscopic current in the direction of the sharp edge 194 shown in the FIG. 6. The spatial extent of this current depends on at least two factors, including the frequency of blade vibrations and viscosity of a fluid. For ultrasonic frequencies in water, the current around the flow generator 188 is localized to an area of several microns. The forces that produce such currents are very strong and can easily overcome the surface tension of water and other fluids, which allows the use this phenomenon to pump fluids like water. Thus, the acoustic streaming from the sharp edge 194 is typically highly localized at the sharp edge with the dimensions that are much smaller than the acoustic wavelength. Because of the sharp edge 194 and the tapering sides 192 of the flow generator 188, the streaming is well localized at the sharp edge and thus does not depend on the overall geometry of the body or the fluid around the body.

FIG. 6 also shows the vector field of the frequency dependent fluid velocity. In some examples, the fluid velocity is observed to be the highest just above the sharp edge 194. The flow pattern consists of the stream directed vertically away from the sharp edge 194 which is fed by the streams coming from the sides. This pattern has proven to be universal for all angles of the sharp edge, fluid viscosities, and frequencies of vibration.

To induce the streaming, the flow generator 188 may be vibrated at its resonance frequency, and in some embodiments may be vibrated at its resonance frequency within a range of about 100 Hz to 10 MHz, for example. In this embodiment, the vibration-generating driving device 106 is driven at the resonance frequency of blade vibrations which is 461 Hz in water. For explanatory purposes, the acoustic motion introduces a boundary layer along the walls of the blade. The boundary layer is a low pressure acoustic force area, and it creates a path for fluid to enter. The fluid enters the acoustic force area along the sides of the wedge and is ejected at the tip driven by the centrifugal force. This results in the streaming pattern from the sharp edge.

In FIGS. 3 and 4, the flow generator 188 is positioned inside the inlet passageway 174 in a manner that directs the jet like streams onto the face of the flexible portion 186. Here, the flow generator 188 is attached to the side walls of the passageway 174. However, other embodiments have the flow generator 188 attached elsewhere, such as the bottom of a chamber or passage. The flow generator geometry is arranged such that it can vibrate perpendicular to its edge (left to right in FIGS. 3-5). The flow generator 188 is driven at its resonance frequency, which as mentioned above, may be a frequency ranging from 100 Hz to 10 MHz, for example. In the example in FIGS. 3 and 4, vibrations of the flow generator 188 are induced by the external driving device 106. In some embodiments, the driving device 106 is an external transducer that vibrates the flow generator 188. In other embodiments, the driving device 106 is an external coil and the flow generator 188 is a magnetic blade. The external coil may then inductively vibrate the flow generator 188 by applying a variable magnetic field to the magnetic blade flow generator. In the example in FIGS. 3 and 4, the driving device 106 is packaged as a separate device that is controlled either by a patient to relieve the symptoms or by a doctor during an office visit. The geometry and frequency of the flow generator 188 can be optimized for a desired flow rate and cracking pressure.

In the embodiment shown, the driving device 106 is arranged to vibrate at the resonance frequency of the flow generator 188. Vibration at the flow generator's resonance frequency causes the flow generator 188 to vibrate more than the surrounding structure of the flow system 160 (or the plate 102 carrying the flow system 160) since the flow system 160 (or plate 102) has a different resonance frequency.

As indicated above, FIG. 3 shows the valve portion 166 in a closed condition, with the acoustic streaming valve arrangement 164 in an off condition. FIG. 4 shows the acoustic streaming valve arrangement 164 in an on or powered condition, creating an acoustic stream of fluid flow in the inlet passageway 174 toward the flexible portion 186.

Because of the forced fluid flow from the sharp edge 194 of the flow generator 188, the fluid acts as a pressure force on the flexible portion 186. When the pressure force exceeds the cracking pressure, the flexible portion 186 deflects as shown in FIG. 4. Thus, with the flexible portion 186 deflected, fluid may flow out of the inlet passageway 174, over the seat 189, and out the outlet passageways 176 for drainage. In addition to opening the flow system 160, the flow generator 188 acts as a pump to draw fluid through the inlet passageway 174 to reduce or lower the IOP in the eye. While the embodiment described above describes vibration of the flow generator 188, in other embodiments, the outer walls of the valve chip 162 may be oscillated while the flow generator 188 remains relatively stationary to create the fluid motion shown in FIG. 6.

In use, the flow system 160 may be opened or closed to regulate IOP in a patient. The plate 102 and drainage tube 104 may be implanted in a patient's eye. The flow system 160 carried on the plate 102 may be controlled manually by placing the driving device 106 either directly against or in the area of the plate 102. In the embodiment shown, the valve portion 166 is closed when the device is in its neutral or closed condition. If the doctor or the patient desires to alleviate IOP or induce flow from the anterior chamber of the eye, the driving device 106 may be activated to vibrate at the resonance frequency of the flow generator 188. In some embodiments, the driving device is placed in contact with the plate 102. This will induce the vibration in the flow generator 188 to generate acoustic streaming toward the flexible portion 186. When the streaming fluid force exceeds the cracking force, the flexible portion 186 deflects, permitting fluid to flow through the flow system 160 and to a drainage site outside the implantable device 100.

When inductive coupling is used to generate vibration, the driving device 106 may not need to contact the implantable device to drive the flow generator 188. Accordingly, the driving device 106 may be placed in the immediate proximity of the flow generator 188, and the flow generator may be vibrated at its resonance frequency.

Figure 7:
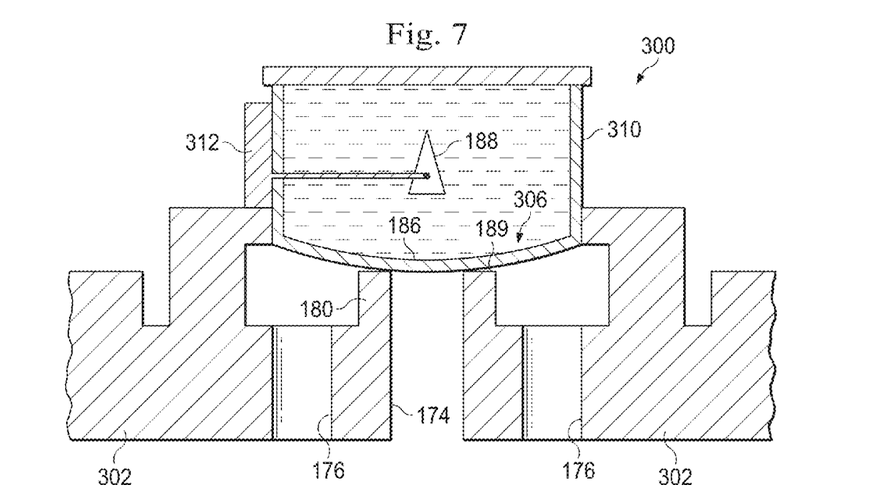
FIG. 7 is an illustration of a cross-sectional view of another exemplary flow system in a closed position according to the principles of the present disclosure.
Figure 8:
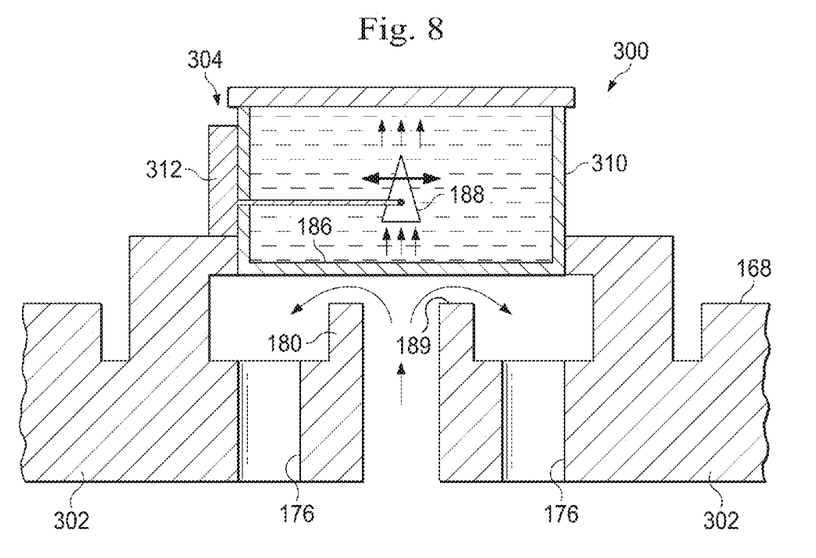
FIG. 8 is an illustration of a cross-sectional view of the flow system in FIG. 7 in an open position according to the principles of the present disclosure.

FIGS. 7 and 8 show another embodiment of an implantable device and flow system 300 that may be carried on or may form a part of the implantable system 100. FIG. 7 shows the flow system 300 in a closed condition that inhibits or prevents fluid flow through the system 300, while FIG. 8 shows the flow system 300 in an open condition, permitting drainage flow through the flow system 300. Because the flow system 300 has many similarities to the flow system 160 discussed above, not all features will be re-described. However, like elements will have like reference numbers.

The flow system 300 includes a valve chip 302, an acoustic streaming valve arrangement 304, and a valve portion 306. The valve chip 302 includes the inlet passageway 174 and the outlet passageway 176. The valve portion 306 includes the boss portion 180, the flexible portion 186, the seat 189, and an actuation chamber 310.

The actuation chamber 310 is a fluid filled chamber and in this embodiment, includes the acoustic streaming valve arrangement 304. Since the acoustic streaming valve arrangement is isolated from the drainage flow through the GDD, the acoustic streaming valve arrangement 304 does not pump fluid through the system. However, it is arranged to open and close the valve portion 306.

The acoustic streaming valve arrangement 304 includes the flow generator 188, and an onboard vibration-inducing driving device 312. The driving device 312 may be configured as discussed above, but may be mechanically connected to the actuation chamber 310, and therefore may take the place of the external driving device 106 shown in FIG. 2. When the driving device 312 is on or is actuated, it induces vibration in the flow generator 188 to move or displace fluid in the actuation chamber 310 away from the flexible portion 186 as shown in FIG. 8. This strong fluid displacement decreases pressure on the chamber-side of the flexible portion 186, thereby permitting the flexible portion 186 to deflect away from the seat 189 and open the flow system 160.

In this embodiment, the flexible portion 186 is still arranged to seat on the boss portion 180 in a neutral or closed condition. Accordingly, until power is applied, the valve portion 306 is still closed since the flexible portion 186 is weighed down by the mass of the fluid in the actuation chamber 310, preventing or inhibiting fluid flow through the flow system 300. However, when the driving device 312 is on or is actuated, the flexible portion 186 may deflect permitting the flow of fluid. A power supply may be on onboard or off-board the system.

Figure 9:
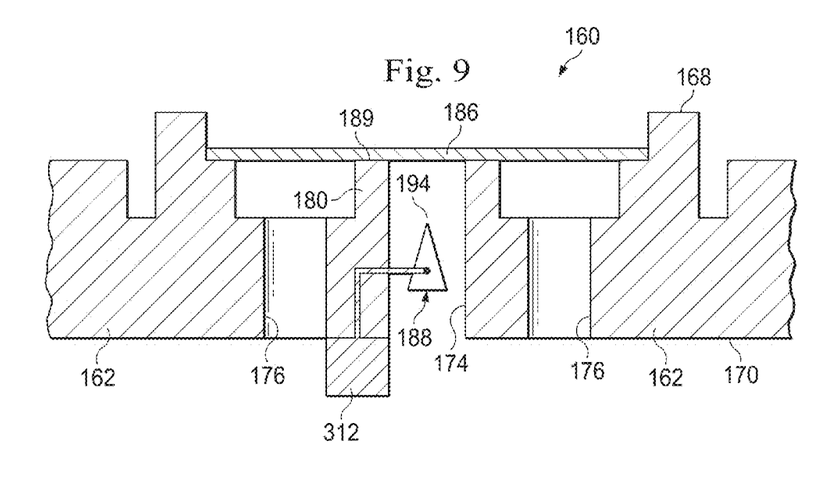
FIG. 9 is an illustration of a cross-sectional view of another exemplary flow system in a closed position according to the principles of the present disclosure.

FIG. 9 shows an arrangement as set forth in FIG. 3 with the flow generator 188 in the inlet passageway 174, but is modified to include the onboard driving device 312. Accordingly, in this embodiment, a patient or doctor does not need to carry a separate driving device. A power source (not shown) may also be included to drive the driving device 312 in the onboard system.

While the embodiments shown disclose systems where the valve portion is biased to the closed condition, other embodiments are contemplated where the valve portion is biased to the open position. In these embodiments, activating the acoustic streaming valve arrangement would close the valve portion and prevent or inhibit fluid flow through the system.

While the embodiments shown include a flow generator that directs the acoustic stream in a direction substantially perpendicular to the surfaces of the flexible portions 186, some embodiments may be customized to orient the acoustic stream in a direction and position such that the overall energy usage is optimized. In addition, this customization may be performed patient to patient, providing a customized treatment to most effectively treat a patient's condition or relieve symptoms of a condition.

The acoustic streaming arrangement disclosure herein creates new opportunities for creating flow systems, such as a fluid valve or a pump system, in an implantable device. This may result in smaller valve-type implants since the acoustic streaming arrangement may be used to open and close the valve. In addition, since the acoustic streaming arrangement has few movable parts, it may be highly reliable. It may be easily integrated with other micro-fluidic circuits, may be relatively easy to manufacture, and may be customizable as it may be tunable to wide range conditions.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

We claim:

1. An acoustic streaming valve arrangement for inducing flow in a glaucoma drainage device, comprising:
    a valve portion configured to selectively inhibit fluid flow between a fluid inlet and a fluid outlet, wherein the valve portion comprises:
        a boss portion including a seat; and
        a flexible portion, wherein the flexible portion selectively and sealingly engages with the boss portion to selectively inhibit fluid flow;
    a selectively vibrating flow generator having a sharp edge; and
    a driving device configured to selectively vibrate the flow generator to create a streaming fluid flow in a direction away from the sharp edge and disengage the flexible portion from the boss portion to open the valve portion to allow fluid flow between the fluid inlet and the fluid outlet.

2. The acoustic streaming valve arrangement of claim 1, wherein the flow generator comprises two nonparallel surfaces forming an angle.

3. The acoustic streaming valve arrangement of claim 2, wherein the two nonparallel surfaces converge to form the sharp edge.

4. The acoustic streaming valve arrangement of claim 2, wherein the sharp edge has an angle of 90 degrees or less.

5. The acoustic streaming valve arrangement of claim 1, wherein the driving device is configured to vibrate the flow generator at the resonance frequency of the flow generator.

6. The acoustic streaming valve arrangement of claim 1, further comprising a flexible portion deflectable by streaming fluid flow to open a valve.

7. An implantable glaucoma drainage system, comprising:
    an inlet passageway and an outlet passageway; and
    a valve portion disposed between the inlet and outlet passageways to regulate the passage of fluid from the inlet passageway to the outlet passageway, the valve portion comprising an acoustic streaming valve arrangement configured to open or close the valve portion, the valve portion further comprising a flexible portion deflectable from a neutral condition to a displaced condition, the valve portion allowing passage of fluid when the flexible portion is in a deflected condition and inhibiting passage of fluid when the flexible point is a neutral condition, the inhibiting caused by sealingly engaging the flexible portion with a boss portion.

8. The implantable glaucoma drainage system of claim 7, wherein the acoustic streaming valve arrangement comprises a flow generator and a driving device configured to vibrate the flow generator, the flow generator being disposed in the inlet passageway.

9. The implantable glaucoma drainage system of claim 7, wherein the flow generator comprises two nonparallel surfaces forming an angle.

10. The implantable glaucoma drainage system of claim 9, wherein the two nonparallel surfaces converge to form a sharp edge.

11. The implantable glaucoma drainage system of claim 10, wherein the sharp edge has an angle of 90 degrees or less.

12. The implantable glaucoma drainage system of claim 10, wherein the sharp edge is an extending edge.

13. The implantable glaucoma drainage system of claim 7, wherein the flexible portion is a membrane.

14. The implantable glaucoma drainage system of claim 7, wherein the acoustic streaming valve arrangement comprises a flow generator and a driving device configured to vibrate the flow generator, the flow generator being disposed in a chamber adjacent the inlet passageway.

15. The implantable glaucoma drainage system of claim 14, wherein the driving device is implantable with the flow generator.

16. A method comprising:
 implanting a flow system in an eye of a patient; and
 activating an acoustic streaming valve arrangement forming a part of the flow system to open or close a valve portion to inhibit or allow drainage fluid to flow through the flow system, wherein opening the valve portion includes causing it to disengage from a boss portion.

17. The method of claim 16, wherein activating an acoustic streaming valve arrangement comprises placing a driving device in the proximity of the flow system to induce vibration in a flow generator of the acoustic streaming valve arrangement.

18. The method of claim 17, wherein activating an acoustic streaming valve arrangement comprises placing the driving device in contact with the flow system to induce vibration in the flow generator.

19. The method of claim 16, comprising deflecting a flexible portion of the flow system with the acoustic streaming valve arrangement to inhibit or allow drainage fluid to flow through the flow system.

* * * * *